United States Patent
Yamamoto et al.

(10) Patent No.: US 7,026,486 B2
(45) Date of Patent: Apr. 11, 2006

(54) PROCESS FOR PRODUCTION CILOSTAZOL

(75) Inventors: Akihiro Yamamoto, Tokushima (JP); Norihiro Fukuyama, Tokushima (JP); Yoshihiko Okaichi, Kitajima (JP); Yasuhiro Yamada, Tokushima (JP); Hisashi Miyamoto, Matsushige (JP); Michiaki Tominaga, Kamiita (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 2 days.

(21) Appl. No.: 10/488,951

(22) PCT Filed: Sep. 9, 2003

(86) PCT No.: PCT/JP03/11515

§ 371 (c)(1),
(2), (4) Date: Mar. 9, 2004

(87) PCT Pub. No.: WO2004/024716

PCT Pub. Date: Mar. 25, 2004

(65) Prior Publication Data

US 2004/0267020 A1      Dec. 30, 2004

(30) Foreign Application Priority Data

Sep. 10, 2002 (JP) ............................. 2002-264314

(51) Int. Cl.
*C07D 215/16* (2006.01)
*C07D 215/20* (2006.01)
(52) U.S. Cl. ...................... 546/158; 546/157
(58) Field of Classification Search ............... 546/158, 546/157
See application file for complete search history.

(56) References Cited

U.S. PATENT DOCUMENTS

| 4,277,479 | A | 7/1981 | Nishi et al. |
| 6,515,128 | B1 * | 2/2003 | Mendelovici et al. ....... 546/158 |
| 6,630,590 | B1 * | 10/2003 | Aki et al. ................... 546/158 |

FOREIGN PATENT DOCUMENTS

| ES | 550434 | 12/1985 |
| JP | 56-45414 | 4/1981 |
| JP | 56-46810 | 4/1981 |
| JP | 58-59980 | 4/1983 |
| JP | 58-077880 | 5/1983 |
| JP | 59-157084 | 9/1984 |
| JP | 1-265051 | 10/1989 |
| JP | 2000-229953 | 8/2000 |
| JP | 2001-213877 | 8/2001 |
| WO | WO 02/14283 A1 | 2/2002 |

OTHER PUBLICATIONS

Nishi, CA 99:98806, Chem & Pharm Bull, 1983, vol. 31(4), pp 1151-1157.*
Nishi, CA 103:141893, Chem & Pharm Bull, vol. 33(3), pp 1140-1147, 1985.*
Nishi; "Research and Development for Platelet Function Inhibitor"; The 29th Symposium on the Chemistry of Natural Products, pp. 41-43, (1994).
Nishi et al.; "Studies on 2-Oxoquinoline Derivatives as Blood Platelet Aggregation Inhibitors. II. 6-[3-(1-Cyclohexyl-5-Tetrazolyl)Propoxy]-1,2-Dihydro-2-Oxoquinoline and Related Compounds"; Chem. Pharm. Bull., vol. 31., No. 4, pp. 1151-1157, (1983).
Nishi et al.; Studies on 2-Oxoquinoline Derivatives as Blood Platelet Aggregation Inhibitors. IV.[1)] Synthesis and Biological Activity of the Metabolites of 6-[4-(1-Cyclohexyl-1H-5-Tetrazolyl)Butoxy]-2-Oxo-1,2,3,4-Tetrahydroquinoline (OPC-13013); Chem. Pharm. Bull. vol. 33, No. 3, pp. 1140-1147, (1985).

* cited by examiner

*Primary Examiner*—D. Margaret Seaman
(74) *Attorney, Agent, or Firm*—Finnegan, Henderson, Farabow, Garrett & Dunner, L.L.P.

(57) ABSTRACT

The present invention provides a process for producing cilostazol [I] in a high yield and a high purity, by reacting a carbostyril derivative [II] with a tetrazole derivative [III] in the presence of an inorganic basic compound in a solvent of water, wherein water is used in an amount of 3 to 7-fold weight to that of the carbostyril derivative [II] and the inorganic basic compound is used in an amount of 1 to 6 mol per mol of the carbostyril derivative [II]. The process of the present invention is the improved and environment-friendly process for producing cilostazol being useful for pharmaceuticals

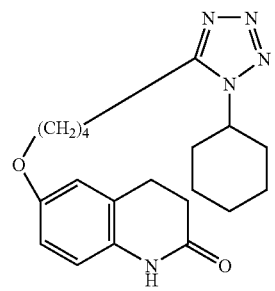

[I]

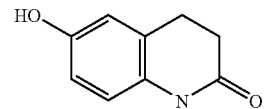

[II]

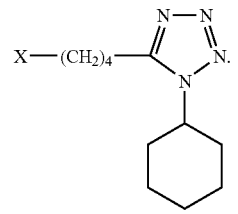

[III]

7 Claims, No Drawings

1

PROCESS FOR PRODUCTION CILOSTAZOL

TECHNICAL FIELD

The present invention relates to a novel process for producing cilostazol represented by the following formula [I]:

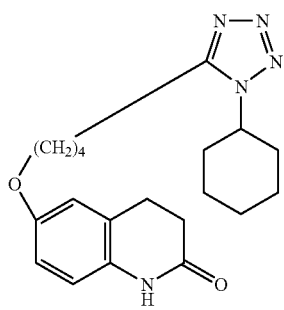

BACKGROUND ART

Cilostazol, prepared according to the present invention, whose chemical name is 6-[4-(1-cyclohexyl-1H-tetrazol-5-yl)butoxy]-3,4-dihydrocarbostyril, is known to be useful as an antithrombotic agent, a cerebral circulation improver, an anti-inflammatory agent, an antiulcer agent, a hypotensive agent, an antiasthmatic agent, and a phosphodiesterase inhibitor, etc. (see e.g. JP-A-56-49378).

As for the process for producing cilostazol, it is known a process comprising a reaction of a carbostyril derivative represented by the following general formula [II]:

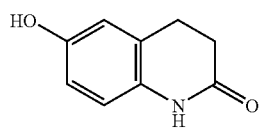

with a tetrazole derivative represented by the following general formula [III]:

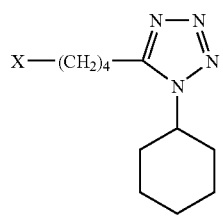

(wherein X represents a halogen atom), in the presence of an inorganic base or an organic base (see e.g. JP-A-56-49378 and Chem. Pharm. Bull., 31(4), 1151–1157 (1983)).

According to the above-mentioned known process, the yield of cilostazol is as low as about 50 to 74%, because there is also formed a compound in which the tetrazole derivative of general formula [III] has reacted not only with the hydroxyl group of the carbostyril derivative of general formula [II] but also with the 1-position of the cilostazol [I] simultaneously. The thus formed contaminative impurity, i.e. the compound in which the 1-position of the cilostazol [I] is substituted by the tetrazole derivative of general formula [III], is difficult to remove. Accordingly, there is a disadvantage of the known process that the production of the cilostazol with a high purity has required a complicated process of purification.

Another process for producing cilostazol, it is known a process comprising a reaction of the above-mentioned carbostyril derivative of the formula [II] with the above-mentioned tetrazole derivative of the formula [III], in the presence of a phase transfer catalyst (see e.g. JP-A-2001-213877 and WO 02/14283).

Yet another process for producing cilostazol, it is proposed a process comprising a reaction of the above-mentioned carbostyril derivative of the formula [II] with the above-mentioned tetrazole derivative of the formula [III], in a non-aqueous hydroxylic solvent in the presence of two kinds of basic compound or in a non-aqueous solvent in the presence of molecular sieves to scavenge water formed as a byproduct (see e.g. WO 02/14283).

However, these known processes inevitably use undesirable materials such as organic solvents and reagents in view of environmental hygiene. On the basis of the growing conscious to international environmental conservation in recent years, great demands become arisen in a chemical industry to make every effort decreasing use of the solvents and reagents pointed out the harmfulness, and preventing those materials from discharging into the environment. In order to fulfil those demands, established processes have to be down for a consideration, alternative raw materials, reagents and solvents being less harmful have to be found out, and the processes having higher conversion rate, yield and selectivity have to be developed; so that the environmental load can be diminished.

Under the circumstances with these social demands, the present inventors have made a study of the process being safer for the environment, for producing cilostazol with using water as a solvent in place of an organic solvent. Heretofore, the chemical reaction has been considered to be efficiently proceeding in the system wherein the reactive substances are dissolved. On the study of the process for producing cilostazol so far, water has never been used as a solvent, since the tetrazole derivative of the formula [III] is absolutely insoluble in water and the tetrazole derivative of the formula [III] is expected to be decomposed in water.

On the other hand, in view of the above-mentioned demands for the environmental hygiene, the present inventors have conducted further studies with the aim of establishing the process using water as a solvent by all means. As a result, the present inventors have found that the objective process is established by applying the specific conditions, and thereby the objects of the present invention can be achieved. Based on this finding, the present invention has been accomplished.

DISCLOSURE OF THE INVENTION

According to the studies made by the present inventors, it has been found that, by using water as a solvent in an amount of 3 to 7-fold weight to that of carbostyril derivative of the formula [II] and by using inorganic basic compounds in an amount of 1 to 6 molar quantity per mol of carbostyril derivative of the formula [II], the reaction for producing cilostazol may proceed without decomposition of the tetrazole derivative of the general formula [III], and besides the formation of the compound in which the 1-position of cilostazol is substituted by the tetrazole derivative of general formula [III] may be suppressed.

That is, the object of the present invention is to provide an improved process for producing the objective cilostazol with high yield and purity, by the reaction of the carbostyril derivative of the formula [II] with the tetrazole derivative of the formula [III], in water as a solvent at the amount of 3 to 7-fold weight to that of carbostyril derivative of the formula [II], in the presence of inorganic basic compounds at the amount of 1 to 6 molar quantity per mol of carbostyril derivative of the formula [II].

Accordingly, it is the object of the present invention to provide a process for producing cilostazol, as a process being safe for environment. It is another object of the present invention to provide a process for producing cilostazol at a low cost and by a simple procedure. It is yet another object of the present invention to provide a process for producing cilostazol without any complicated process of purification, in a high yield, and in a high purity. It is yet another object of the present invention to provide an industrially advantageous process for producing cilostazol.

According to the process of the present invention, by using environment-friendly water as a solvent, the objective cilostazol can be produced on an industrial scale, at a low cost, by a simple procedure, in a high yield and in a high purity. Thus, the process of the present invention is of great worth as a process for producing cilostazol being useful for pharmaceuticals industrially.

BEST MODE FOR CARRYING OUT THE INVENTION

The improved process for producing cilostazol of the present invention is further explained in detail below.

The process of the present invention is indicated as the following reaction scheme-1.

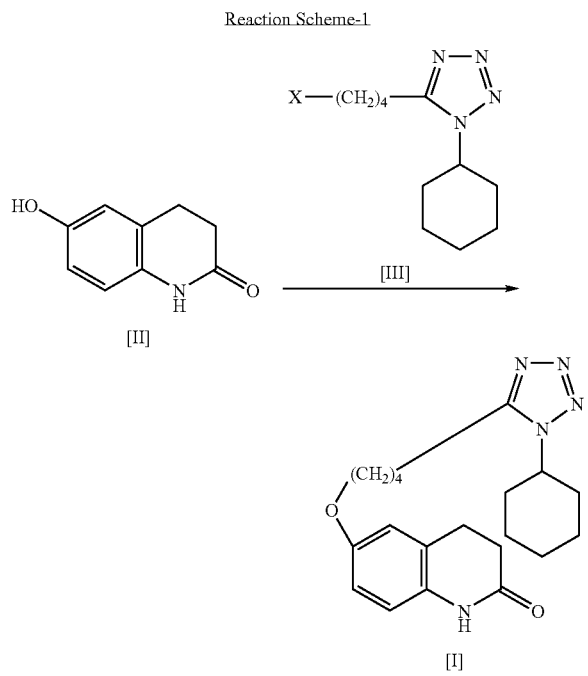

(wherein X is a halogen atom selected from the group consisting of a fluorine atom, a chlorine atom, a bromine atom and an iodine atom, among which particularly preferred is a chlorine atom).

In the reaction scheme-1 the reaction between a carbostyril derivative of the formula [II] and a tetrazole derivative of the general formula [III] is carried out in water at the amount of 3 to 7-fold weight to that of carbostyril derivative of the formula [II], in the presence of inorganic basic compounds at the amount of 1 to 6 molar quantity per mol of carbostyril derivative of the formula [II].

As the inorganic basic compound, known ones can be used extensively. Examples thereof include inorganic bases such as sodium hydroxide, potassium hydroxide, cesium hydroxide, lithium hydroxide, sodium carbonate, potassium carbonate, cesium carbonate, lithium carbonate, lithium hydrogen carbonate, sodium hydrogen carbonate, potassium hydrogen carbonate, silver carbonate and the like; alkali metals such as sodium, potassium and the like; and mixtures thereof. In case of using one kind of inorganic basic compound alone, any one of the alkaline metal carbonates selected from the group consisting of sodium carbonate, potassium carbonate, cesium carbonate, lithium carbonate, lithium hydrogen carbonate, sodium hydrogen carbonate, potassium hydrogen carbonate and the like is particularly preferred, and the preferable amount thereof is 1 to 6 mol per mol of the carbostyril derivative [II], particularly preferable 1 to 5 mol per mol of the carbostyril derivative [II]. In case of using two or more kinds of inorganic basic compound by mixture, a mixture of one or two or more alkaline metal hydroxides selected from the group consisting of sodium hydroxide, potassium hydroxide, cesium hydroxide, lithium hydroxide and the like; and one or two or more alkaline metal hydroxides selected from the group consisting of sodium carbonate, potassium carbonate, cesium carbonate, lithium carbonate, lithium hydrogen carbonate, sodium hydrogen carbonate, potassium hydrogen carbonate and the like is particularly preferred. In case of using the mixture, the amount of the alkaline metal hydroxide to be used is 0.4 to 1 mol, preferably 0.4 to 0.9 mol per mol of the carbostyril derivative [II], and the amount of the alkaline metal carbonate to be used is 1 to 5 mol, preferably 2 to 5 mol per mol of the carbostyril derivative [II]. When using the mixture, the total amount of the inorganic basic compounds is usually 1 to 6 mol, preferably 1 to 5 mol per mol of the carbostyril derivative [II].

The reaction is carried out usually at a temperature not lower than ambient temperature and not higher than 200° C., and preferably at a temperature of 50 to 150° C. The reaction time is usually from about one hour to about 20 hours. It is recommended to use the tetrazole derivative [III] usually in an amount of at least 0.5 mol, preferably 0.5 to 1.5 mol, and more preferably 1.1 to 1.5 mol per mol of the carbostyril derivative [II].

In the above-mentioned reaction, a lower alcohol may be added to the reaction system in a certain amount thereof which does not affect environment. For example, a lower alcohol such as methanol, ethanol, propanol, isopropyl alcohol, butanol, ethylene glycol or the like may be added in an amount of 5 to 30% by volume to the amount of water. Further, sodium sulfite, sodium thiosulfate or the like may be added to the reaction system of the above-mentioned reaction for the purpose of preventing the coloration caused by oxidation.

The reaction may be carried out with circulating the reaction mixture by continuous disperser. The reaction mixture is repeatedly introduced into the continuous disperser and pulverized therein, then returned to the reaction vessel so as to circulate the reaction mixture constantly. The circulation of the reaction mixture can prevent the crystals of the objective product of cilostazol from adhering with each other to make big agglomerates.

Cilostazol of the formula [I] obtained by the above-mentioned reaction can be easily isolated by the conventional separating means. As said separating means, mention can be made of, for example, method comprising cooling the reaction mixture, followed by collecting the crystals by filtration; method comprising heating the crystals and washing it with alcohol such methanol or the like, followed by distilling off the solvent and cooling so as to obtain the crystals; extraction method using a solvent; dilution method; recrystallization method; column chromatography; preparative thin layer chromatography; etc.

EXAMPLES

Next, the process of the present invention is more specifically explained below with reference to examples.

The purity of the products obtained in the examples was determined by high performance liquid chromatography (HPLC) under the following conditions.

Detector: Ultraviolet rays absorptiometer
Column: equivalent of YMC-pack SIL 120A
Eluent: $CH_2Cl_2$:n-hexane:MeOH=20:10:1
Flow rate: about 1.0 ml/min.
Wavelength detected: 254 nm Example 1

Into a reaction vessel having a capacity of 500 mL were introduced 6-hydroxy-3,4-dihydrocarbostyril (30 g, 0.18 mol), 1-cyclohexyl-5-(4-chlorobutyl)-1,2,3,4-tetrazole (49.09 g, 0.20 mol, 1.1 M), potassium carbonate (55.90 g, 0.40 mol, 2.2 M), sodium hydroxide (5.88 g, 0.15 mol, 0.8 M), sodium sulfite (1.5 g, 0.01 mol) and purified water (150 ml). The mixture of the reactants was heated at about 92° C. for about 6 hours with circulating by continuous disperser (pipeline homomixer T.K.ROBO MIX manufactured by TOKUSHUKIKA KOGYO CO. LTD.). After the completion of the reaction, the reaction mixture was cooled to around 50° C., and the mixture was introduced into a flask having a capacity of 1 L, methanol (150 mL) was added thereto and the resulting reaction mixture was refluxed with heating for about 2 hours. The mixture was cooled to the ambient temperature and the precipitated crystalline product was collected by filtration and washed with purified water (150 mL), methanol (90 mL), followed by purified water (150 mL), then dried at about 80° C. Thus, 62.14 g of cilostazol was obtained. Yield: 91.48%, Purity: 99.66%, m.p.: 158–159° C.

Example 2

Into a flask having a capacity of 200 mL were introduced 6-hydroxy-3,4-dihydrocarbostyril (12 g, 0.07 mol), 1-cyclohexyl-5-(4-chlorobutyl)-1,2,3,4-tetrazole (19.64 g, 0.08 mol), potassium carbonate (22.36 g, 0.16 mol), sodium hydroxide (2.35 g, 0.05 mol), sodium sulfite (0.6 g, 0.004 mol) and purified water (60 mL). The mixture of the reactants was heated at about 92° C. for about 6 hours. After the completion of the reaction, the reaction mixture was cooled to around 50° C., and the deposited crude crystals were once collected by filtration. The crystals obtained were introduced into a flask and purified water (120 mL) was added thereto, then the crystals were washed with stirring at about 85° C. for about 15 minutes. The reaction mixture was cooled to around 50° C., and the precipitated crystals were collected by filtration. The crystals obtained were introduced into a flask again and methanol (84 mL) was added thereto, then the crystals were washed with stirring at about 25° C. for about 15 minutes. The reaction mixture was cooled to 10° C. or less, the precipitated crystalline product was collected by filtration and washed with methanol (24 mL), then dried at about 80° C. Thus, 24.15 g of cilostazol was obtained. Yield: 88.88%, Purity: 99.50%, m.p.: 158–159° C.

Example 3

Into a reaction vessel having a capacity of 500 mL were introduced 6-hydroxy-3,4-dihydrocarbostyril (30 g, 0.18 mol), 1-cyclohexyl-5-(4-chlorobutyl)-1,2,3,4-tetrazole (49.1 g, 0.20 mol, 1.1 M), potassium carbonate (83.84 g, 0.61 mol, 3.3 M), sodium sulfite (1.5 g, 0.01 mol) and purified water (150 mL). The mixture of the reactants was heated at about 85° C. for about 6 hours with circulating by continuous disperser (pipeline homomixer T.K.ROBO MIX manufactured by TOKUSHUKIKA KOGYO CO. LTD.). After the completion of the reaction, the reaction mixture was cooled to around 50° C. and the deposited crude crystals were once collected by filtration. The crystals obtained were introduced into a flask having a capacity of 1 L and purified water (300 mL) was added thereto, then the crystals were washed with stirring at about 85° C. for about 15 minutes. After washing the crystals, the reaction mixture was cooled to around 50° C. and the precipitated crystals were collected by filtration. The crystals obtained were introduced into a flask again and methanol (210 mL) was added thereto, then the crystals were washed with stirring at about 25° C. for about 15 minutes. The reaction mixture was cooled to 10° C. or less, the precipitated crystalline product was collected by filtration and washed with methanol (60 mL), then dried at about 80° C. Thus, 62.79 g of cilostazol was obtained. Yield: 92.44%, Purity: 99.61%, m.p.: 158–159° C.

Example 4

Into a flask having a capacity of 200 ml were introduced 6-hydroxy-3,4-dihydrocarbostyril (12 g, 0.07 mol), 1-cyclohexyl-5-(4-chlorobutyl)-1,2,3,4-tetrazole (19.64 g, 0.08 mol, 1.1 M), potassium carbonate (33.54 g, 0.24 mol, 3.3 M), sodium sulfite (0.6 g, 0.004 mol) and purified water (60 mL). The mixture of the reactants was heated at about 85° C. for 6 hours. After the completion of the reaction, the reaction mixture was cooled to around 50° C., and the precipitated crystals were collected by filtration. The crystals obtained were introduced into a flask, and purified water (120 mL) was added thereto, then the crystals were washed with stirring at about 85° C. for about 15 minutes. After washing the crystals, the reaction mixture was cooled to around 50° C. and the precipitated crystals were collected by filtration. The crystals obtained were introduced into a flask again and methanol (84 mL) was added thereto, and the crystals were washed with stirring at about 25° C. for about 15 minutes. The reaction mixture was cooled to 10° C. or less, the precipitated crystalline product was collected by filtration and washed with methanol (24 mL), then dried at about 80° C. Thus, 24.28 g of cilostazol was obtained. Yield: 89.36%, Purity: 99.44%, m.p.: 158–159° C.

Example 5

Into a flask having a capacity of 200 ml were introduced 6-hydroxy-3,4-dihydrocarbostyril (12 g, 0.07 mol), 1-cyclohexyl-5-(4-chlorobutyl)-1,2,3,4-tetrazole (19.64 g, 0.08 mol), potassium carbonate (22.36 g, 0.16 mol), sodium hydroxide (2.35 g, 0.05 mol), sodium sulfite (0.6 g, 0.004 mol), purified water (36 mL) and isopropanol (3.6 mL), and the reaction was conducted for about 6 hours under reflux. After the completion of the reaction, the reaction mixture was cooled to around 10° C., and the precipitated crystals were collected by filtration. The crystals obtained were introduced into a flask, and purified water (120 mL) was added thereto, then the crystals were washed with stirring at about 85° C. for about 15 minutes. The reaction mixture was cooled to around 50° C. and the precipitated crystals were collected by filtration. The crystals obtained were introduced into a flask again and methanol (84 mL) was added thereto, then the crystals were washed with stirring at about 25° C. for about 15 minutes. The reaction mixture was cooled to 10° C. or less, the precipitated crystalline product was collected by filtration and washed with methanol (24 mL), then dried at about 80° C. Thus, 24.31 g of cilostazol was obtained. Yield: 89.47%, Purity: 99.45%, m.p.: 158–159° C.

The invention claimed is:

1. A process for producing cilostazol represented by the following general formula [I]:

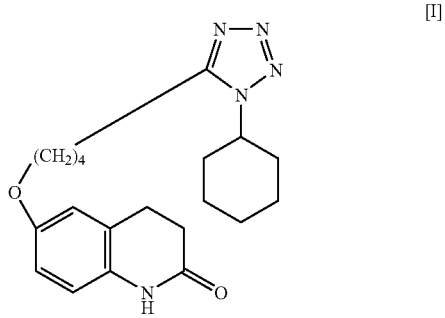

which comprises reacting a carbostyril derivative represented by the following general formula (II):

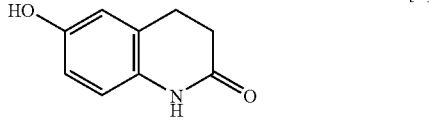

with a tetrazole derivative represented by the following general formula (III):

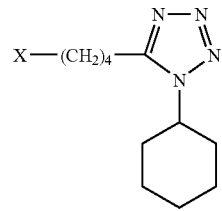

(wherein X represents a halogen atom), in the presence of an inorganic basic compound in a solvent of water,
   wherein water is used in an amount of 3 to 7-fold weight to that of the carbostyril derivative [II] and the inorganic basic compound is used in an amount of 1 to 6 mol per mol of the carbostyril derivative [II].

2. The process according to claim 1, wherein said inorganic basic compound is selected from the group consisting of inorganic bases of sodium hydroxide, potassium hydroxide, cesium hydroxide, lithium hydroxide, sodium carbonate, potassium carbonate, cesium carbonate, lithium carbonate, lithium hydrogen carbonate, sodium hydrogen carbonate, potassium hydrogen carbonate and silver carbonate; alkali metals of sodium and potassium; and mixtures thereof.

3. The process according to claim 2, wherein said inorganic basic compound is one kind of alkaline metal carbonate selected from the group consisting of sodium carbonate, potassium carbonate, cesium carbonate, lithium carbonate, lithium hydrogen carbonate, sodium hydrogen carbonate and potassium hydrogen carbonate.

4. The process according to claim 2, wherein said inorganic basic compound is a mixture of one or two or more alkaline metal hydroxides selected from the group consisting of sodium hydroxide, potassium hydroxide, cesium hydroxide and lithium hydroxide; and one or two or more alkaline metal carbonates selected from the group consisting of sodium carbonate, potassium carbonate, cesium carbonate, lithium carbonate, lithium hydrogen carbonate, sodium hydrogen carbonate and potassium hydrogen carbonate.

5. The process according to claim 4, wherein the amount of said alkaline metal hydroxides to be used is 0.4 to 1 mol per mol of the carbostyril derivative [II], and the amount of said alkaline metal carbonates to be used is 1 to 5 mol per mol of the carbostyril derivative [II].

6. The process according to claim 1, wherein the amount of the tetrazole derivative [III] to be used is at least 0.5 mol per mol of the carbostyril derivative [II].

7. The process according to claim 1, wherein X is a chlorine atom.

* * * * *